(12) United States Patent
Henderson et al.

(10) Patent No.: US 9,597,452 B2
(45) Date of Patent: Mar. 21, 2017

(54) AUTOINJECTOR

(71) Applicant: Sanofi-Aventis Deutschland GmbH, Frankfurt am Main (DE)

(72) Inventors: Charley Henderson, Cambridgeshire (GB); David Cross, Hertfordshire (GB); Douglas Ivan Jennings, Hertfordshire (GB); Ryan Anthony McGinley, Cambridgeshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/412,405

(22) PCT Filed: Jun. 28, 2013

(86) PCT No.: PCT/EP2013/063726
§ 371 (c)(1),
(2) Date: Dec. 31, 2014

(87) PCT Pub. No.: WO2014/005955
PCT Pub. Date: Jan. 9, 2014

(65) Prior Publication Data
US 2015/0157790 A1   Jun. 11, 2015

(30) Foreign Application Priority Data

Jul. 6, 2012 (EP) ................................. 12175347

(51) Int. Cl.
*A61M 5/172* (2006.01)
*A61M 5/20* (2006.01)
(Continued)

(52) U.S. Cl.
CPC .......... *A61M 5/172* (2013.01); *A61M 5/1456* (2013.01); *A61M 5/158* (2013.01); *A61M 5/20* (2013.01); *A61M 5/24* (2013.01); *A61M 2005/004* (2013.01); *A61M 2005/1585* (2013.01); *A61M 2005/31588* (2013.01); *A61M 2205/3576* (2013.01);
(Continued)

(58) Field of Classification Search
CPC ................ A61M 5/008; A61M 5/2033; A61M 5/31546; A61M 2005/004; A61M 2005/206; A61M 2205/609; A61M 2205/35; A61M 2205/502; A61M 2205/52; A61M 5/1456; A61M 5/145; A61M 2005/14573
See application file for complete search history.

(56) References Cited

U.S. PATENT DOCUMENTS

2007/0233001 A1* 10/2007 Burroughs ............ A61M 5/008
  604/131
2008/0312604 A1* 12/2008 Boesen ................. A61M 5/008
  604/207

FOREIGN PATENT DOCUMENTS

WO    2005097237 A1   10/2005
WO    2008107889 A2   9/2008
WO    2009027950 A2   3/2009

* cited by examiner

*Primary Examiner* — Nathan R Price
*Assistant Examiner* — Melissa A Snyder
(74) *Attorney, Agent, or Firm* — Fish & Richardson P.C.

(57) ABSTRACT

Described is a cartridge comprising a case adapted to detachably engage an autoinjector, an ampoule containing a medicament, and a needle magazine containing a plurality of double-tipped needle assemblies. An autoinjector comprises the cartridge, a housing adapted to detachably engage the cartridge and a user interface adapted to provide visual, audible or tactile feedback.

18 Claims, 4 Drawing Sheets (51) Int. Cl.
*A61M 5/24* (2006.01)
*A61M 5/145* (2006.01)
*A61M 5/158* (2006.01)
A61M 5/00 (2006.01)
A61M 5/315 (2006.01)

(52) U.S. Cl.
CPC . *A61M 2205/505* (2013.01); *A61M 2205/581* (2013.01); *A61M 2205/583* (2013.01)

AUTOINJECTOR

CROSS REFERENCE TO RELATED APPLICATIONS

The present application is a U.S. National Phase application pursuant to 35 U.S.C. §371 of International Application No. PCT/EP2013/063726 filed Jun. 28, 2013, which claims priority to European Patent Application No. 12175347.9 filed Jul. 6, 2012. The entire disclosure contents of these applications are herewith incorporated by reference into the present application.

FIELD OF INVENTION

The invention relates to an autoinjector for administering a medicament.

BACKGROUND

Administering an injection is a process which presents a number of risks and challenges for users and healthcare professionals, both mental and physical. Injection devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Autoinjectors may be mechanical, electro-mechanical or fully electronic. Conventional mechanical autoinjectors may automatically provide the required force for needle insertion and medicament delivery, but may not provide additional functionality (e.g., alignment verification, injection site verification, etc.) which may be capable with electro-mechanical and fully electronic autoinjectors.

Thus, there remains a need for an improved autoinjector.

SUMMARY

It is an object of the present invention to provide an improved autoinjector.

In an exemplary embodiment, a cartridge according to the present invention comprises a case adapted to detachably engage an autoinjector, an ampoule containing a medicament; and a needle magazine containing a plurality of double-tipped needle assemblies.

In an exemplary embodiment, the cartridge further comprises a needle booting device adapted to remove a needle boot coupled to a given one of the needle assemblies. The needle booting device is adapted to replace the needle boot on the given one of the needle assemblies.

In an exemplary embodiment, the cartridge further comprises a memory adapted to store data about the ampoule, the medicament, the needle magazine, or the needle assemblies.

In an exemplary embodiment, the cartridge further comprises a connector adapted to allow reading data from and writing data to the memory.

In an exemplary embodiment, an autoinjector according to the present invention comprises a cartridge as described herein, a housing adapted to detachably engage the cartridge, and a user interface adapted to provide visual, audible or tactile feedback.

In an exemplary embodiment, the autoinjector further comprises a data processing unit.

In an exemplary embodiment, the autoinjector further comprises a first motor adapted to rotate the needle magazine to align a needle assembly with the ampoule.

In an exemplary embodiment, the autoinjector further comprises a second motor adapted to operate the needle booting device.

In an exemplary embodiment, the autoinjector further comprises a third motor adapted to displace the ampoule relative to the cartridge for needle insertion and retraction and to displace a plunger to engage a stopper in the ampoule for medicament delivery.

In an exemplary embodiment, the autoinjector further comprises a sensor detecting placement of the autoinjector on an injection site.

In an exemplary embodiment, the autoinjector further comprises a communication device adapted to transmit and receive data to and from an external computing device.

In an exemplary embodiment, the autoinjector further comprises an energy source including a disposable battery or a rechargeable battery.

In an exemplary embodiment, the user interface is a display screen, a light emitting diode, a speaker, a microphone, a touch screen, a button.

In an exemplary embodiment, the plunger rod is flexible.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
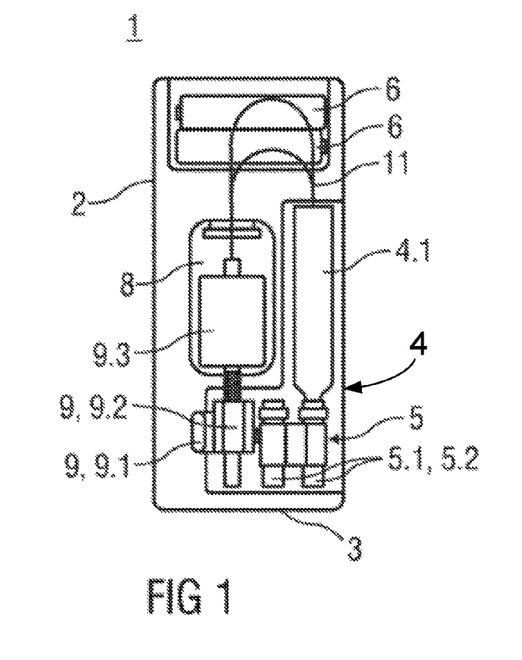
FIG. 1 is a schematic front view of an exemplary embodiment of an autoinjector according to the present invention.

FIG. 1 is a schematic front view of an exemplary embodiment of an autoinjector 1 according to the present invention. The autoinjector 1 comprises a housing 2. In an exemplary embodiment, the housing 2 includes a door which is adapted to open (e.g., by sliding or hingedly), receive a cartridge, close and lock. In another exemplary embodiment, the housing 2 may include an exposed connector adapted to engage the cartridge. The cartridge may contain, for example, an ampoule, one or more needles, a syringe, a needle magazine, a plunger, a needle assembly replacement device, a needle boot removal device, and a needle boot replacement device.

In an exemplary embodiment, the housing 2 includes a distal end 3 which is adapted to be disposed on an injection site. The distal end may have a contoured (e.g., curved) surface to facilitate alignment of the autoinjector 1 and stability during the injection.

In an exemplary embodiment, a cartridge 4 may be utilized with the autoinjector 1. The cartridge 4 may be replaceable, allowing the housing 2 to be used repeatedly. In an exemplary embodiment, the cartridge 4 includes a case containing an ampoule 4.1 containing a medicament, a needle magazine 5 including a plurality of needle assemblies 5.1, a needle assembly replacement device and a needle booting device. In another exemplary embodiment, the cartridge 4 may include an ampoule displacement device in place of the needle replacement device. The needle assemblies 5.1 may be single-use, double-tipped needle assemblies which have distal tips that are initially covered by needle boots 5.2. A proximal tip may be adapted to pierce a septum on the ampoule 4.1. In an exemplary embodiment, a number of needle assemblies 5.1 in the cartridge 4 corresponds to a number of doses intended to be provided by the ampoule 4. In an exemplary embodiment, the needle booting device comprises a hook adapted to engage and disengage a needle boot 5.2, and a rotator for displacing the needle boot 5.2 relative to an longitudinal axis of the needle assembly 5.1.

In an exemplary embodiment, the autoinjector 1 comprises an energy source 6 and a data processing unit 8. The energy source 6 may be one or more disposable batteries (e.g., alkaline) or a rechargeable battery (e.g., Li ion). In the latter case, the autoinjector 1 may include a port for coupling to a permanent power source (e.g., a wall outlet) for recharging the battery. The data processing unit 8 may include a microprocessor and memory (e.g., ROM, RAM or any combination thereof). The data processing unit 8 may include software (e.g., firmware) which includes instructions for operating the autoinjector 1.

The cartridge 4 may comprise a memory for storing data related to the cartridge 4 and its contents (e.g., type and volume of the medicament, expiration date, etc.) and exchanging and/or authenticating data with the data processing unit 8 of the autoinjector 1. For example, the data processing unit 8 may prevent operation of the autoinjector 1 if the cartridge 4 cannot be authenticated.

In an exemplary embodiment, the cartridge 4 may include a temperature sensor, such as a thermistor (not illustrated), for generating data indicative of a temperature of the medicament. The temperature data may be sent to the cartridge memory to be communicated to the data processing unit 8.

In an exemplary embodiment, the autoinjector 1 includes a user interface, such as a display screen 8 and one or more buttons 13, or a touch screen. The user interface may allow a user to visually, audibly, tactilely and/or orally interact with the autoinjector 1. The user interface may provide functionality including, but not limited to, configuring/editing a user profile for the patient, family member and/or healthcare provider, configuring operational parameters (e.g., needle insertion depth, injection speed/force, medicament, etc.), saving and responding to feedback about the injection, displaying instructions for use of the autoinjector.

In an exemplary embodiment, one or more sensors may be disposed adjacent the distal end 3 of the autoinjector 1 for detecting a presence of an injection site. The sensors may also generate data which the data processing unit 8 may utilize to determine whether the site is good for an injection (e.g., whether the site has veins, scar tissue, etc.).

The autoinjector 1 comprises one or more motors 9 for performing motions related to the injection. In an exemplary embodiment, three motors 9 are utilized. A first motor 9.1 is adapted to interact with the needle magazine 5 to rotate and position the needle assemblies 5.1 relative to the ampoule 4.1. In another exemplary embodiment, the first motor 9.1 may interact with the ampoule displacement device for positioning the ampoule 4.1 with relative to a given one of the needle assemblies 5.1 A second motor 9.2 may to interact with the needle booting device in the cartridge 4 to deboot an unused needle assembly 5.1 and reboot a used needle assembly 5.1 A third motor 9.3 may be arranged to displace the ampoule 4 relative to the cartridge 4 for needle penetration and retraction and for advancing a plunger 11 into and out of the ampoule 4.1 for dispensing the medicament. In an exemplary embodiment, the motors 9, 9.1, 9.2, 9.3 may include gear trains to reduce the output speed of the motors 9, 9.1, 9.2, 9.3 and to increase their torque in order to deliver the required motions and forces.

Figure 2:
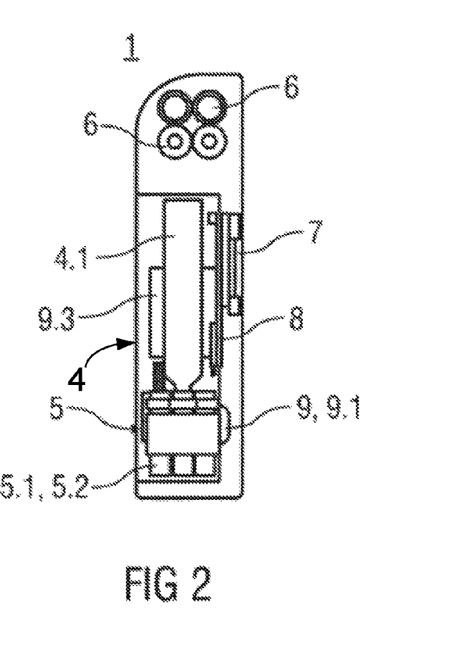
FIG. 2 is a schematic lateral view an exemplary embodiment of an autoinjector according to the present invention.
Figure 3:
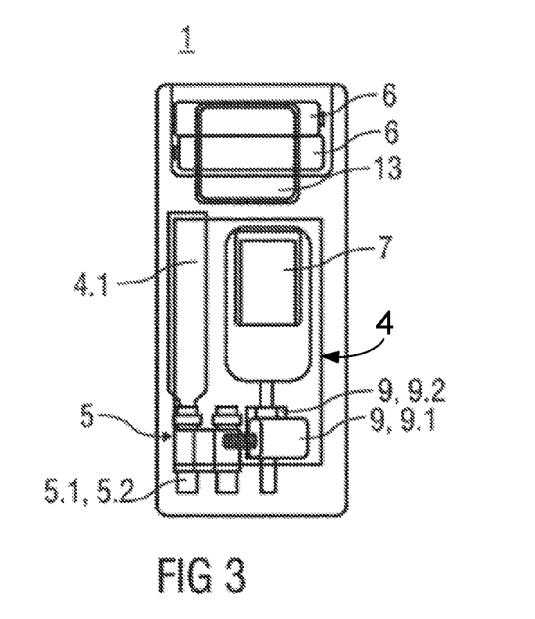
FIG. 3 is a schematic rear view an exemplary embodiment of an autoinjector according to the present invention.

In an exemplary embodiment, the plunger 11 may be arranged as a resilient rod that is adapted to bend such that a first portion interacts with the third motor 9.3 and a second portion engages the ampoule 4.1 (and/or the stopper therein). As shown in FIGS. 1-3, the plunger 11 may be configured in a U-shape to reduce a form factor of the autoinjector 1 and such that axial movement of the first portion in a first direction results in axial movement of the second portion in a second direction opposite the first direction. Those of skill in the art will understand that the third motor 9.3 and the plunger 11 may utilize a rack and pinion mechanism. In an exemplary embodiment, the autoinjector 1 includes an encoder (or other position sensor) to detect a position of the plunger 11.

In an exemplary embodiment, the autoinjector 1 may include a communication device adapted for wired and/or wireless communication. For example, the autoinjector 1 may a have USB port, Ethernet port or other connector, or a wireless radio adapted for communication according to one or more wireless protocols (e.g., cellular, 802.1x, RFID, Bluetooth, etc.).

Figure 4:
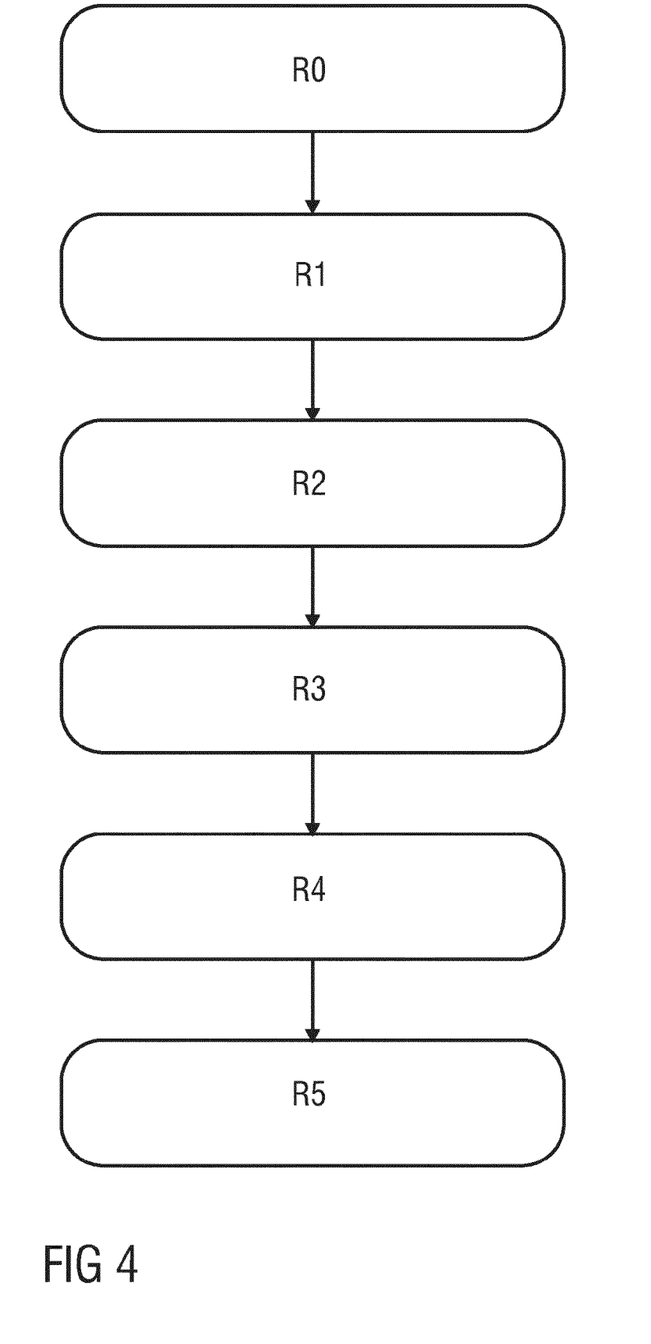
FIG. 4 is an exemplary embodiment of a method for initializing an autoinjector according to the present invention.

FIG. 4 shows an exemplary embodiment of a method for initializing an autoinjector according to the present invention.

In step R0, the autoinjector 1 is powered-on. Those of skill in the art will understand that, in this step R0, the autoinjector 1 may be switched from a no-power mode to a power-mode or may be switched from a stand-by, low-power mode to an operational mode.

In step R1, the autoinjector 1 performs various authentication procedures to verify components of the autoinjector 1. For example, the data processing unit 8 may verify that the energy source 6 is authentic and may verify that the cartridge 4 (if it is coupled to the autoinjector 1) is authentic.

In step R2, the autoinjector 1 may establish a communication link with a remote database. For example, the data processing unit 8 may transmit and/or receive data to/from the database. The data may include, for example, authentication data for an authorized user(s) of the autoinjector 1, a treatment protocol, etc.

In step R3, a cartridge 4 is coupled to the autoinjector 1. Those of skill in the art will understand that, as described above, a cartridge 4 may have multiple doses and/or needles, and thus need not be disengaged from the autoinjector 1 after each injection. The cartridge 4 may engage the autoinjector 1 via a coupling mechanism disposed on each, e.g., threads, snaps, shape-fit, etc. To remove the cartridge 4, the autoinjector 1 may include an eject button, which disengages the coupling mechanisms. For example, the coupling mechanism may include latches disposed on the case which engage resilient hooks on the housing 2 of the autoinjector 1. The eject button, when pressed, may disengage the latches from the hooks.

In step R4, the autoinjector 1 may authenticate the cartridge 4. For example, the data processing unit 8 may read data from a memory device (e.g., ROM) or indicia (e.g., barcode) and compare the data to authorized cartridge data stored in memory. This step may further include determining whether the cartridge 4 is prepared for an injection, e.g., whether sufficient needle assemblies 5.1 are included, whether all motors 9, 9.1, 9.2, 9.3 are operational, whether the temperature and/or date of the medicament is suitable, etc. In an exemplary embodiment, if the cartridge 4 or any other parameter associated with the cartridge 4 or the medicament is not verified, the display screen 8 may notify the user that a new cartridge is required.

In step R5, the autoinjector 1 may indicate visually and/or audibly that it may be used to administer an injection.

Figure 5:
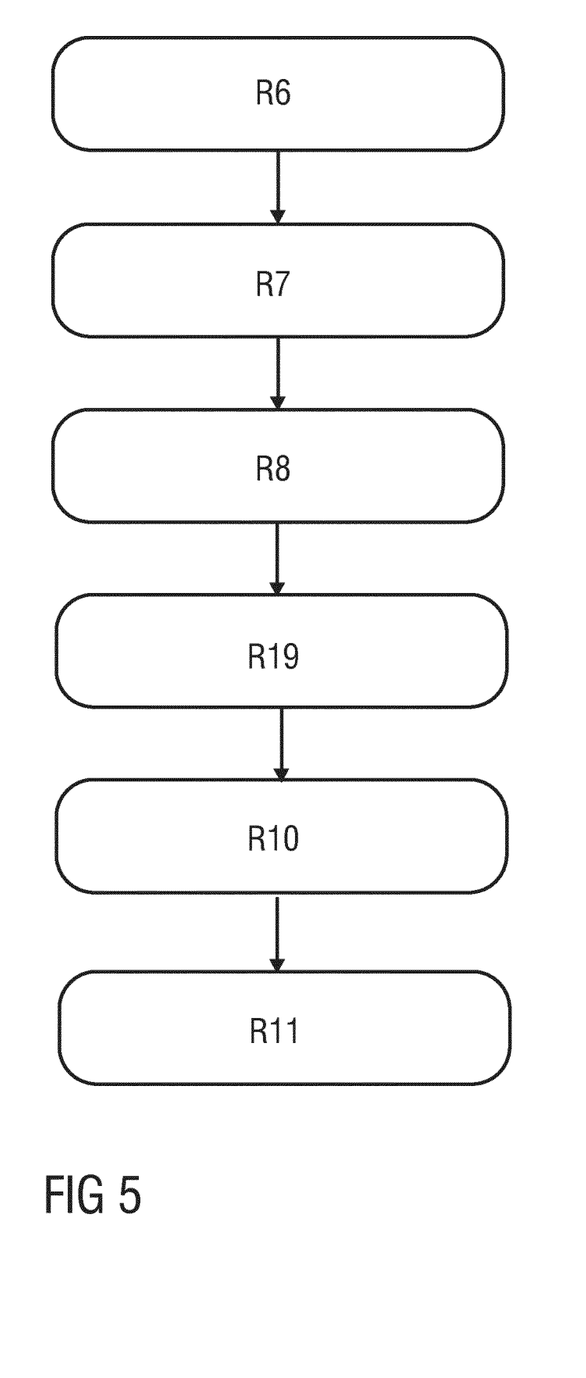
FIG. 5 is an exemplary embodiment of a method for preparing an autoinjector according to the present invention.

FIG. 5 shows an exemplary embodiment of a method for preparing an autoinjector 1 for an injection according to the present invention.

In step R6, the autoinjector 1 initiates an injection procedure. For example, the user may interact with the display screen 7 and/or press the button 13 to indicate that he/she is ready to perform an injection, to enter a selected dose, to adjust injection settings (e.g., to indicate an injection site location on his/her body), etc. The user may be prompted to interact with the display screen 7 when the data processing unit 8 indicates that a scheduled injection time is reached. The autoinjector 1 may also confirm via the sensor on the distal end 3 of the autoinjector 1 that the autoinjector 1 is placed on a suitable injection site. In an exemplary embodiment, the autoinjector 1 may suspend the injection procedure if the autoinjector 1 is removed from the injection site.

In step R7, the autoinjector 1 prompts the user to authenticate him/herself. For example, the display screen 7 may provide a message which requests that the user provide some identifying indicia, e.g., a PIN code, a biometric indicia, etc.

In step R8, the autoinjector 1 activates the first motor 9.1 to rotate the needle magazine 5 to align an unused needle assembly 5.1 with the ampoule 4.1. In another exemplary embodiment, activation of the first motor 9.1 may operate the ampoule displacement device to align the ampoule 4.1 with an unused needle assembly 5.1.

In step R9, the autoinjector 1 activates the second motor 9.2 to operate the needle booting device to deboot the unused needle assembly 5.1.

In step R10, the cartridge data may be updated to indicate that the selected needle assembly 5.1 cannot be re-used.

In step R11, the autoinjector 1 notifies the user that it is ready to perform an injection.

In any one or more of the above steps, feedback may be provided via the user interface to indicate the action(s) being taken by the autoinjector 1. For example, messages may be provided via the display screen 7 which indicate that the needle assembly 5.1 is being selected.

Figure 6:
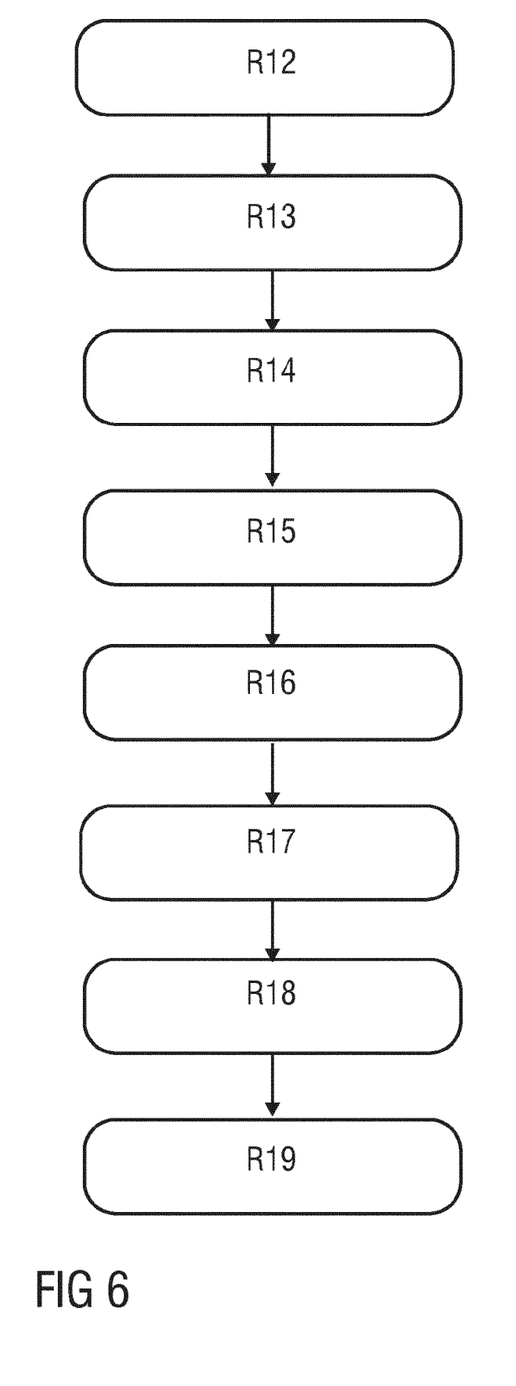
FIG. 6 is an exemplary embodiment of a method for performing an injection with an autoinjector according to the present invention.

FIG. 6 shows an exemplary embodiment of a method for performing an injection with an autoinjector 1 according to the present invention.

In step R12, the autoinjector 1 initiates the injection. For example, the user may press the button 13 or the display screen 7, or the injection may begin automatically after a predetermined time (e.g., N seconds after the autoinjector 1 has been on the injection site and the needle assembly 5.1 has been selected and aligned with the ampoule 4.1).

In step R13, the autoinjector 1 activates the third motor 9.3 for needle penetration. For example, the plunger 11 may be advanced to push the ampoule 4.1 to engage the needle assembly 5.1. After the needle assembly 5.1 is engaged to the ampoule 4.1, the assembly may translate toward the distal end 3 of the autoinjector 1 and the needle assembly 5.1 may be inserted into the injection site to a predetermined depth. One of the one or more sensors in the autoinjector 1 may confirm that the needle assembly 5.1 has been inserted based on displacement of the ampoule 4.1 and/or the plunger 11 from its respective initial position.

In step R14, the autoinjector 1 activates the third motor 9.3 for dispensing the medicament. For example, the plunger 11 may be advanced to push the stopper in the ampoule 4.1 to dispense the medicament through the needle assembly 5.1 into the injection site. One of the one or more sensors in the autoinjector 1 may confirm that the intended dose has been delivered based on displacement of the plunger 11 from its position after the needle penetration.

In step R15, the autoinjector 1 activates the third motor 9.3 for needle retraction. For example, the ampoule 4.1, with needle assembly 5.1 attached, may be translated away from the distal end 3 of the autoinjector 1. Further translation of the ampoule 4.1 in the proximal direction disengages the proximal point of the needle 5.1 assembly from the ampoule 4.1. One of the one or more sensors in the autoinjector 1 may confirm that the needle assembly 5.1 has been retracted based on displacement of the ampoule 4.1 and/or the plunger 11 from its respective position after the needle penetration.

In step R16, the autoinjector 1 may activate the second motor 9.2 to operate the needle booting device to reboot the used needle assembly 5.1.

In step R17, the autoinjector 1 indicates that the injection is complete. For example, the user interface may provide feedback (visual, audible and/or tactile) to notify the user that the injection is complete.

In any one or more of the above steps, feedback may be provided via the user interface to indicate the action(s) being taken by the autoinjector 1. For example, messages may be provided via the display screen 7 to indicate the progress of the injection, time remaining, etc.

In an exemplary embodiment, the autoinjector 1 may emit sounds and/or display content on the display screen 7 so as to reassure the user during the injection or distract them from anticipation of pain.

In step R18, the autoinjector 1 may record data about the completed (or incomplete) injection. For example, the data processing unit 4 may generate data indicating whether the injection was complete, the date, the time, the dose, the user, etc. The data may be stored in memory and/or sent to the database which may log the injection data.

In step R19, the autoinjector 1 may provide feedback about the status of the cartridge 4. For example, if the ampoule 4.1 is empty or the needle assemblies 5.1 are used, the display screen 7 may generate a message prompting the user to replace the cartridge 4.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A cartridge comprising:
a case;
an ampoule disposed in the case and containing a medicament;
a needle magazine disposed in the case, the needle magazine containing a plurality of double-tipped needle assemblies, the needle magazine comprising a needle boot covering a distal tip of a needle assembly; and
a needle booting device disposed in the case, the needle booting device adapted to remove the needle boot coupled to the needle assembly,
wherein the case of the cartridge is adapted to detachably engage an autoinjector such that the autoinjector is operable to
engage the needle assembly with the ampoule,
interact with the needle booting device to remove the needle boot from the distal tip of the needle assembly, and
provide a force to dispense the medicament from the ampoule through the needle assembly.

2. The cartridge according to claim 1, wherein the needle booting device is adapted to replace the needle boot on the needle assembly.

3. The cartridge according to claim 1, further comprising: a memory adapted to store data about the ampoule, the medicament, the needle magazine, or the needle assemblies.

4. The cartridge according to claim 3, further comprising: a connector to connect with the autoinjector to allow reading data from and writing data to the memory.

5. The cartridge according to claim 1, wherein the needle magazine comprises a plurality of needle boots covering distal tips of the needle assemblies.

6. An autoinjector comprising:
a cartridge comprising
a case,
an ampoule disposed in the case and containing a medicament,
a needle magazine disposed in the case and containing a plurality of double-tipped needle assemblies, the needle magazine comprising a needle boot covering a distal tip of a needle assembly, and
a needle booting device disposed in the case, the needle booting device adapted to remove the needle boot coupled to the needle assembly;
a housing adapted to detachably engage the case of the cartridge, wherein the autoinjector is operable to engage the needle assembly with the ampoule, interact with the needle booting device to remove the needle boot from the distal tip of the needle assembly, and provide a force to dispense the medicament from the ampoule through the needle assembly when the housing of the autoinjector engages the case of the cartridge; and
a user interface adapted to provide visual, audible or tactile feedback.

7. The autoinjector according to claim 6, further comprising a data processing unit.

8. The autoinjector according to claim 6, further comprising a motor adapted to rotate the needle magazine to align the needle assembly with the ampoule.

9. The autoinjector according to claim 6, further comprising a motor adapted to operate the needle booting device to remove the needle boot from the distal tip of the needle assembly.

10. The autoinjector according to claim 6, further comprising a motor adapted to displace the ampoule relative to the cartridge for needle insertion and retraction and to displace a plunger to engage a stopper in the ampoule for medicament delivery.

11. The autoinjector according to claim 6, further comprising: a sensor detecting placement of the autoinjector on an injection site.

12. The autoinjector according to claim 6, further comprising:
a communication device adapted to transmit and receive data to and from an external computing device.

13. The autoinjector according to claim 6, further comprising: an energy source including a disposable battery or a rechargeable battery.

14. The autoinjector according to claim 6, wherein the user interface is a display screen, a light emitting diode, a speaker, a microphone, a touch screen, or a button.

15. The autoinjector according to claim 6, further comprising a plunger rod to advance into the ampoule to dispense the medicament, wherein the plunger rod is flexible.

16. The autoinjector according to claim 6, wherein the needle magazine comprises a plurality of needle boots covering distal tips of the needle assemblies.

17. The autoinjector according to claim 6, further comprising a drive mechanism configured to:
operate the needle booting device to engage the needle boot and rotate the needle boot relative to a longitudinal axis of the needle assembly, and
translate the needle assembly toward a distal end of the autoinjector for needle insertion and to translate the needle assembly away from the distal end of the autoinjector for needle retraction.

18. The autoinjector according to claim 6, wherein:
the cartridge comprises a first memory adapted to store cartridge data, and
the autoinjector comprises a data processing unit configured to communicate with a second memory storing authorized cartridge data, the data processing unit being adapted to
compare the cartridge data to the authorized cartridge data to attempt authentication of the cartridge,
enable operation of the autoinjector if the authentication is successful, and
disable operation of the autoinjector if the authentication is not successful.

* * * * *